United States Patent [19]

Mozes et al.

[11] Patent Number: 5,058,514
[45] Date of Patent: Oct. 22, 1991

[54] PROCESS FOR CONTROLLING ACID GAS EMISSIONS IN POWER PLANT FLUE GASES

[76] Inventors: Miriam S. Mozes, 58 Clarinda Drive, Willowdale, Ontario, Canada, M2K 2W3; Rene Mangal, 793 Shaw Street, Toronto, Ontario, Canada, M6G 3L9; Raja Thampi, 6049 Grossbeak Drive, Mississauga, Ontario, Canada, L5N 5W9

[21] Appl. No.: 583,210

[22] Filed: Sep. 17, 1990

Related U.S. Application Data

[63] Continuation-in-part of Ser. No. 423,782, Oct. 18, 1989.
[51] Int. Cl.$^5$ .................. F23J 11/00; F23J 15/00
[52] U.S. Cl. ..................... 110/345; 110/344; 423/235; 423/239; 423/244
[58] Field of Search ............ 110/342, 345, 344; 423/235, 239, 244; 55/22

[56] References Cited

U.S. PATENT DOCUMENTS

| | | | |
|---|---|---|---|
| 4,325,924 | 4/1982 | Arand et al. | 423/235 |
| 4,555,996 | 12/1985 | Torbov et al. | 110/345 |
| 4,851,201 | 7/1989 | Heap et al. | 423/235 |

Primary Examiner—Edward G. Favors
Attorney, Agent, or Firm—Ridout & Maybee

[57] ABSTRACT

An in-furnace sorbent slurry injection process for the simultaneous control of $SO_2$ and $NO_x$ from power plant flue gases is described. An aqueous slurry of limestone or dolomite-doped limestone and a nitrogenous progenitor compound is injected into the furnace at temperatures ranging between 900° C. and 1350° C. Under optimized operating conditions, with urea selected as the nitrogenous progenitor, about 80% of the $SO_2$ and 90% of the $NO_x$ are simultaneously removed.

10 Claims, 14 Drawing Sheets

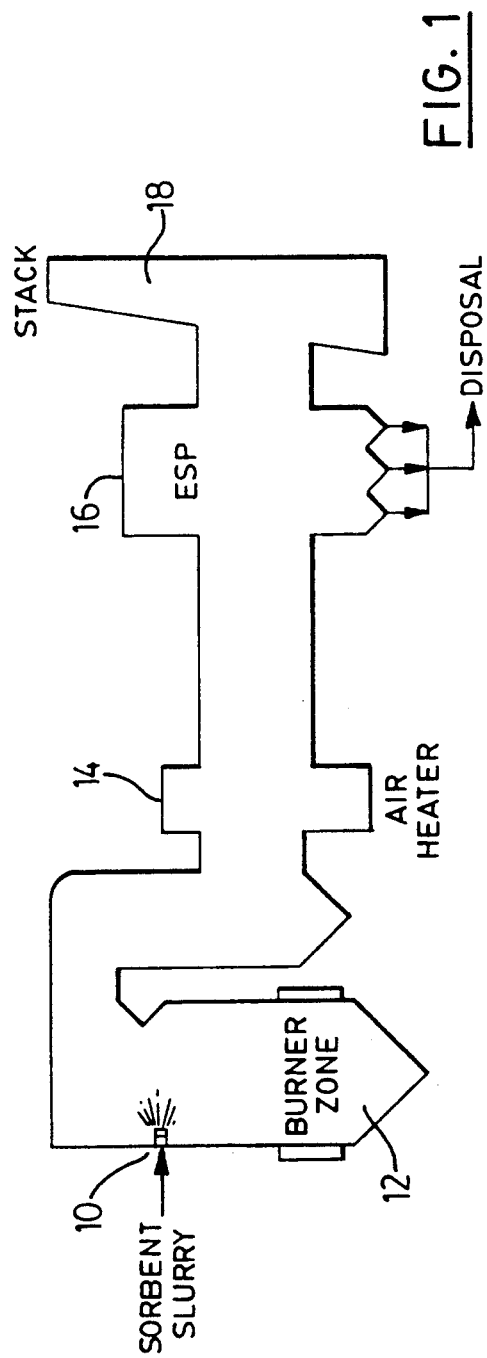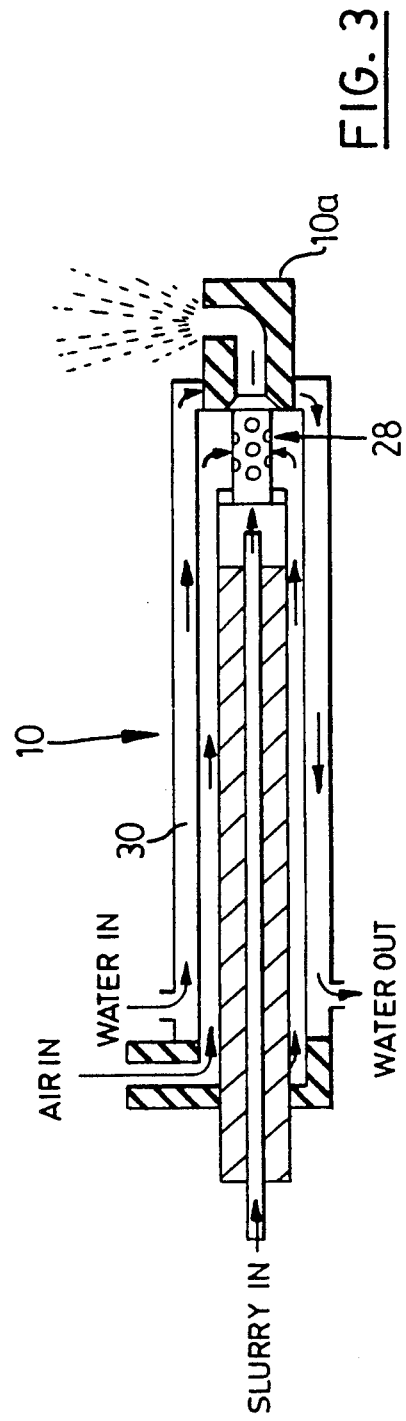

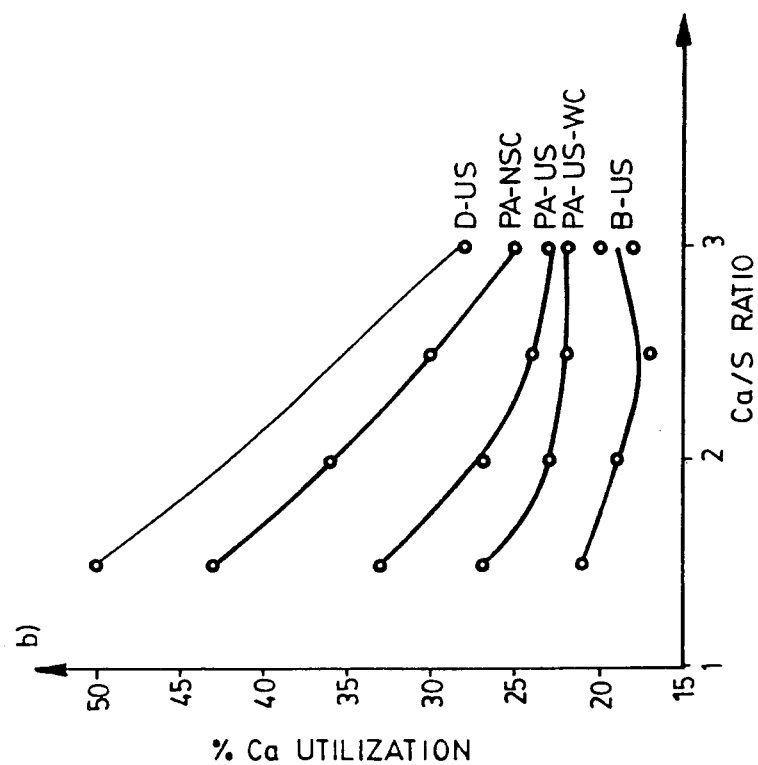
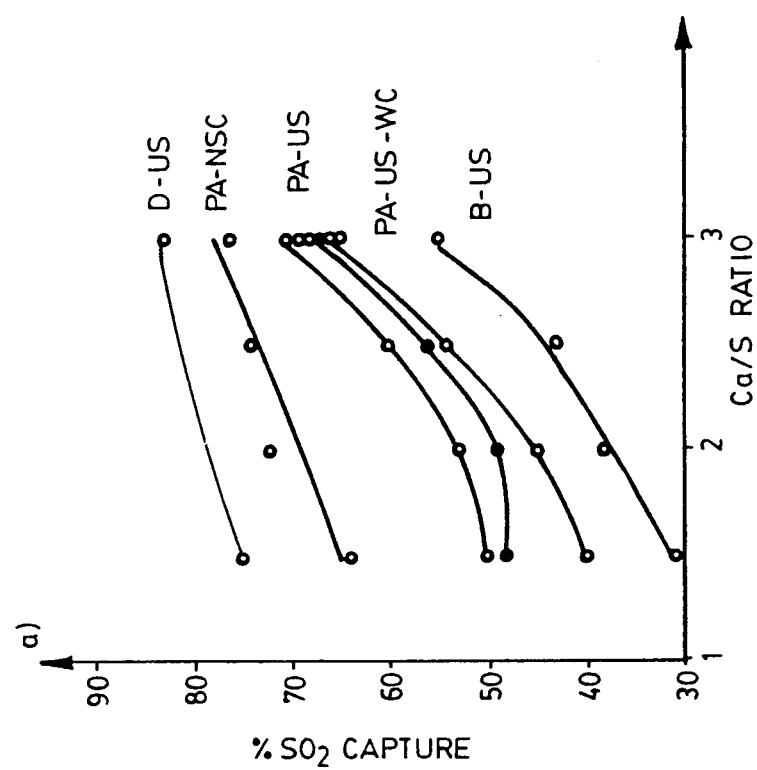
FIG. 7a
FIG. 7b

PROCESS FOR CONTROLLING ACID GAS EMISSIONS IN POWER PLANT FLUE GASES

This application is a continuation-in-part of U.S. patent application Ser. No. 07/423,782 filed Oct. 18, 1989 and entitled "Process for Controlling Acid Gas Emissions in Power Plant Flue Gases".

The invention relates to an integrated process for the simultaneous reduction of $SO_2$ and $NO_x$ in combustion gases, particularly utility boiler and incinerator flue gases. The mixed oxides of nitrogen herein referred to as $NO_x$ include nitric oxide, nitrogen dioxide and nitrous oxide.

In the electrical power system of many utilities, such as Ontario Hydro, a substantial portion of the electrical energy generated is produced in coal-burning plants. Such facilities provide an important element of flexibility in conjunction with hydraulic and nuclear generators, the importance of which increases during periods of peak demand and when demand exceeds the predicted level. However, combustion effluents and waste products from coal-burning stations are a source of acid gas pollutants, those of chief concern being sulphur dioxide and nitrogen oxides.

There have been many efforts directed to the removal of nitric oxide from combustion effluents. NO is the oxide of nitrogen that tends to predominate in high temperature combustion waste gases and cannot readily be removed by conventional scrubbing techniques.

U. S. Pat. No. 3,900,554 (Lyon) describes the selective reduction of NO in a combustion element by dosing the effluent stream with ammonia or ammonia precursors such as ammonium salts, and aqueous solutions thereof.

Canadian patent No. 1,089,195 (Azubata et al.) describes a process for removing nitrogen oxides from a gas by adding a reducing agent selected from the group consisting of ammonia, an ammonium salt, an amine and an amide, and additionally hydrogen peroxide to the gas at a temperature in the range of 400° C. to 1200° C., thereby decomposing the nitrogen oxides to nitrogen gas and water.

U. S. Pat. No. 4,208,386 (Arand) discloses a process for selectively reducing $NO_x$ in a combustion effluent containing $NO_x$ by contacting the effluent stream in the presence of oxygen with urea or urea solution at a temperature in the range of about 870 C to 1110 C.

There is likewise a large body of prior art directed to the removal of sulphur oxides, chiefly $SO_2$, from combustion effluents, based on various modes of introducing chemical additives such as calcium carbonate, magnesium carbonate, limestone, dolomite, and calcium hydroxide, which react with $SO_2$ so as to cause sorption on these particulate materials at elevated temperatures.

Some of the prior art relating to $SO_2$ reduction is reviewed in U.S. Pat. No. 4,555,996 (Torbov), which itself discloses the spray injection of a slurry of calcium carbonate into a first zone outside the combustion zone of a conventional J-shaped gas furnace at temperatures above about 1200.C and at an experimentally determined location in the furnace such that the sprayed composition is dried to particles in a cooler second zone, where sulphur dioxide is bound to the sorbent particles. The measurements disclosed in Torbov were, however, carried out not with coal but in a pilot scale test furnace fired by a mixture of natural gas plus hydrogen sulphide, intended to simulate the combustion of coal having a sulphur content of approximately 3%.

To date, there have been no practical and efficient techniques for the simultaneous removal of both sulphur and nitrogen oxides from the exhaust gases formed by burning sulphur- and nitrogen-bearing fossil fuels and wastes in boilers or incinerators. A problem encountered in attempts to develop a truly integrated system is that some of the possible additives for the removal of $NO_x$ are chemically incompatible with the sorbents used to remove $SO_2$.

Further, even where the active agents for the separate $NO_x$ and $SO_2$ removal processes do not actually interfere with each other, it is not necessarily the case that operating conditions optimal for the one pollutant removal reaction will also be best for the other. U.S. Pat. No. 659,996 issued July 25, 1989 to Heap et al. discloses the sequential removal of $NO_x$ and $SO_x$ from a combustion effluent stream by first introducing an $NO_x$-reducing agent into a fuel-rich, oxygen-deficient "gaseous decomposition zone" at a first temperature range, followed by introduction of the reacted gaseous mixture into an oxygen-rich "reaction zone" where an $SO_x$-removal agent is introduced at a second temperature range.

We have discovered that the simultaneous removal of both kinds of contaminant can be effected by using an aqueous slurry of a fine particulate calcium based sorbent containing a "compatible" $NO_x$-removing additive which forms reactive radicals in the temperature "window" in which the sulphation reaction takes place. Many known additive compounds which react with $NO_x$ outside this temperature window, between about 900° C. and about 1350° C., are unsuitable for integrating the removal of both $SO_2$ and $NO_x$.

It is accordingly an object of the present invention to provide an integrated process for simultaneously reducing the sulphur dioxide, nitric oxide and other acidic components from flue gases produced by the combustion of fossil fuels in combustion installations such as utility and industrial boilers and waste incinerators.

According to the process of the invention, $SO_2$ and $NO_x$ removal may be simultaneously effected by injecting an aqueous slurry of a fine particulate calcium based sorbent containing a selected compatible nitrogen-based additive through an atomizing nozzle into a coal-burning furnace at temperatures ranging from 900° C. to 1350° C., where the slurry is injected in the form of a spray of very fine droplets of a size up to about 150 $\mu$m mass median diameter (MMD) which are well dispersed within the flue gas stream to ensure good distribution and intimate mixing of the sorbent-additive mixture with the flue gas.

The slurry droplet size is "boiler-specific", in that the optimum size to ensure efficient transport of the reagents and their distribution and mixing with the flue gas to maximize reactivity will vary with the boiler type, dimensions and configuration. In the pilot scale coal-fired furnace installation described below, an optimum droplet size for the atomized aqueous slurry composition was in the range of 3-17 $\mu$m MMD, but larger droplet sizes are required for full scale boilers. The optimum droplet size range may readily be arrived at by empirical testing or by computation of an optimal size range with the aid of physical models, whereby boiler dimensions, configuration, type and aerodynamics are coupled with the parameters of the particular spray nozzle used.

Sorbent and additives are introduced into the furnace at stoichiometric ratios of between 1.5 and 3.0 moles of sorbent calcium per mole of $SO_2$ and at least 1.5 moles of additive per mole of $NO_x$.

The technique prevents deactivation of the sorbent at the temperatures of injection and allows for sufficient residence time at favourable temperatures for the reaction between $SO_2$ and sorbent and $NO_x$ and additive to be efficiently completed. With suitable additives, which may be referred to as "nitrogenous progenitors", the additive/$NO_x$ and sorbent/$SO_2$ reactions proceed substantially independently and are subject to mutually compatible optimum operation conditions.

Urea has been found to be a preferred nitrogenous progenitor additive. Optimal simultaneous capture of $SO_2$ and $NO_x$ was achieved by adding urea to an aqueous slurry of sorbent and carrying out the process under conditions for the optimum capture of both pollutants. Under such optimized operating conditions, up to 83% of the $SO_2$ and 90% of the $NO_x$ can be simultaneously removed from a typical flue gas stream.

Another useful nitrogenous progenitor is ammonium carbonate. Data discussed below shows that under optimized operating conditions $SO_2$ removal of up to 75% is achieved with simultaneous $NO_x$ removal up to about 85%.

The combination of limestone slurry with ammonia as the nitrogenous progenitor was found to be rather less efficient for the simultaneous removal of sulphur and nitrogen oxides than either urea or ammonium carbonate, with maximum $SO_2$ and $NO_x$ captures of 58% and 64%, respectively. Examples of other nitrogenous progenitors for use in the simultaneous removal of $SO_2$ and $NO_x$ according to the process of the invention include ammonium salts other than carbonate, cyanuric acid, etc.

Further and other objectives and advantages of the present invention will be apparent from the following specification and accompanying drawings, in which:

FIG. 1 is a schematic drawing of a typical coal-fired furnace installation including means for injecting a sorbent slurry;

FIG. 3 is a detailed sectional view of the slurry atomizer nozzle used in the sorbent injection system of the apparatus of FIG. 2;

Figure 4B:
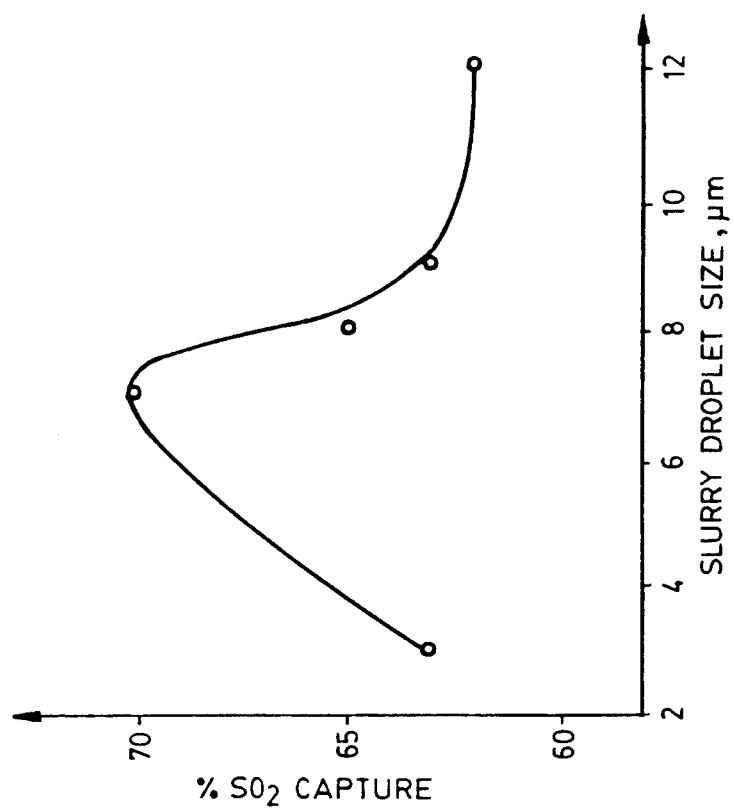
Figure 4A:
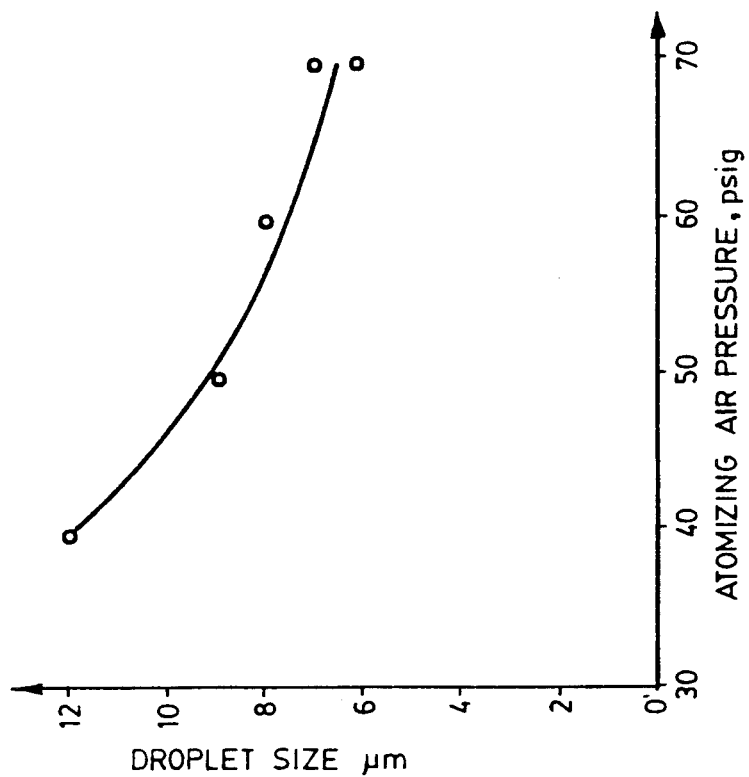
Figure 5:
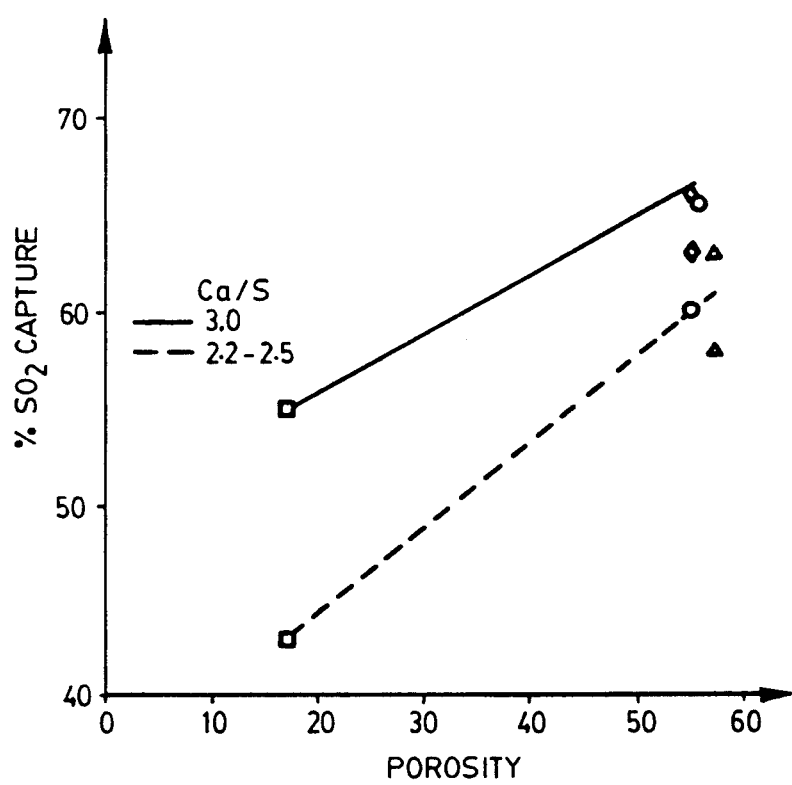
Figure 6B:
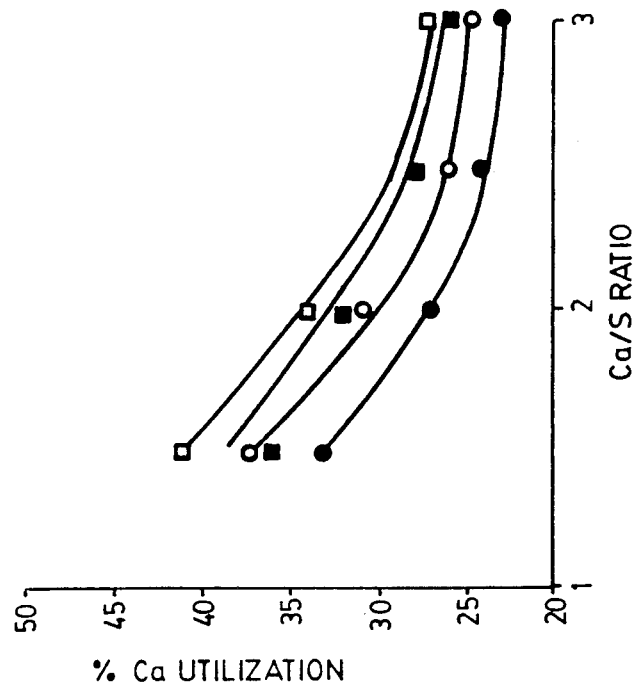
Figure 6A:
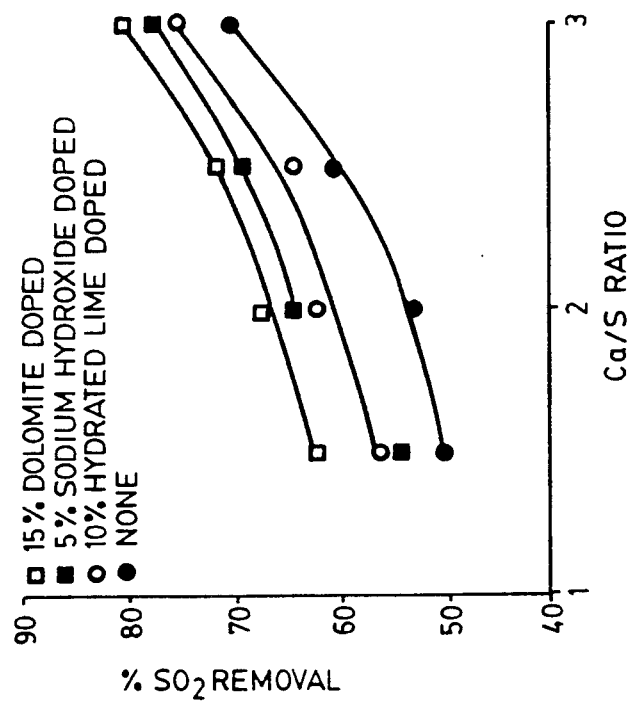
Figure 8B:
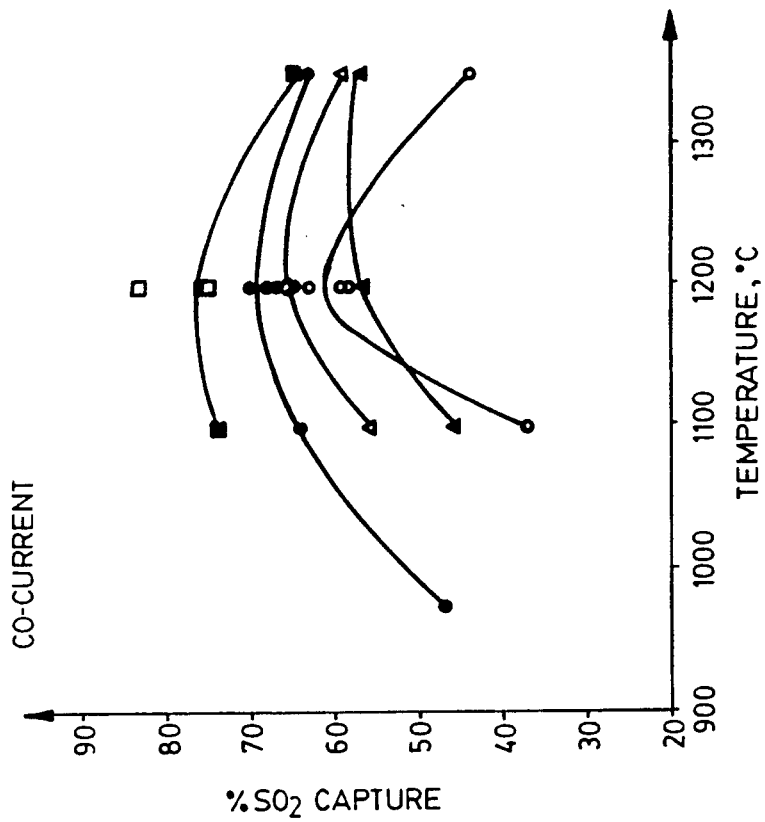
Figure 8A:
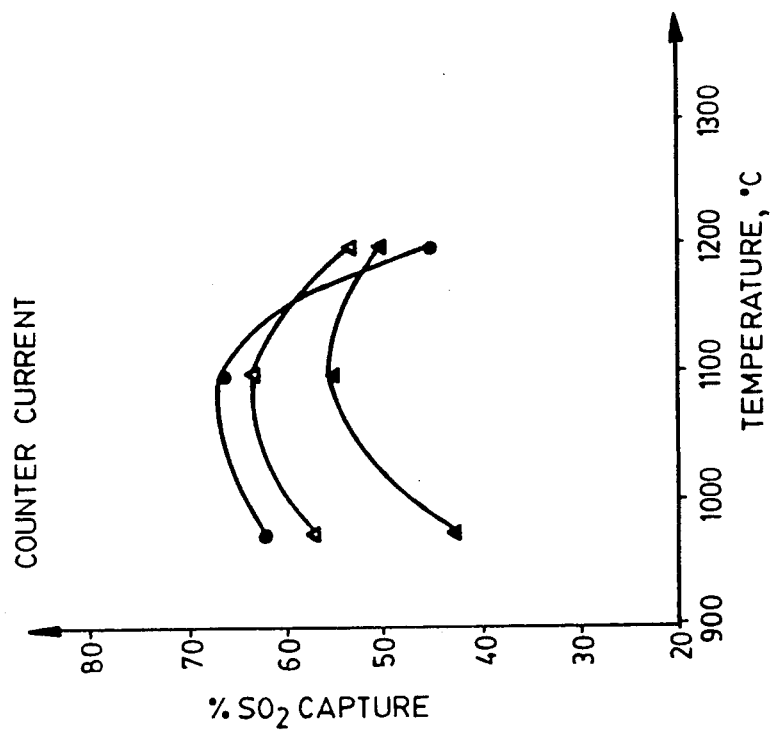
Figure 9:
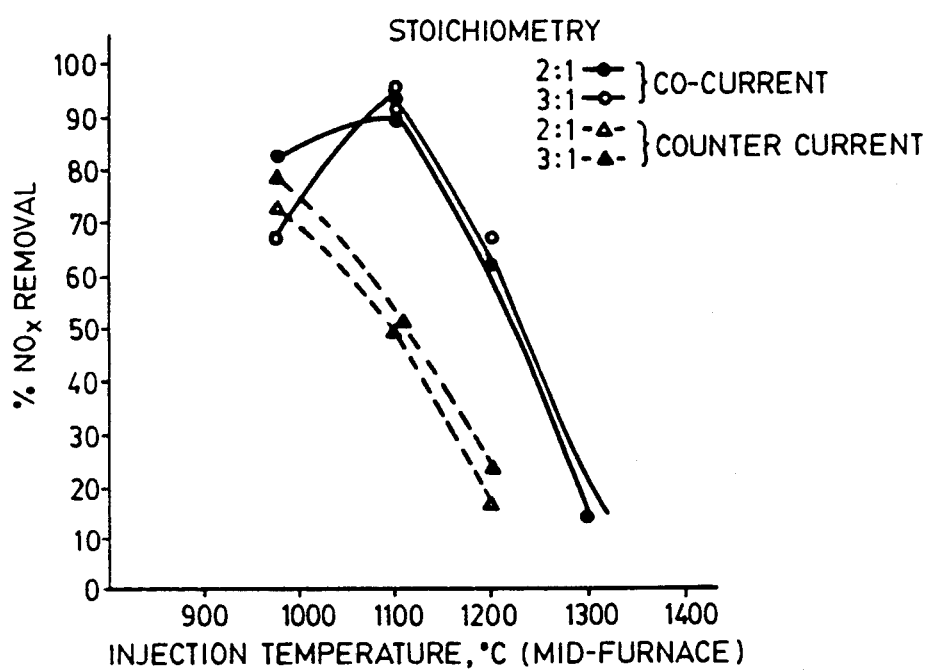
Figure 10B:
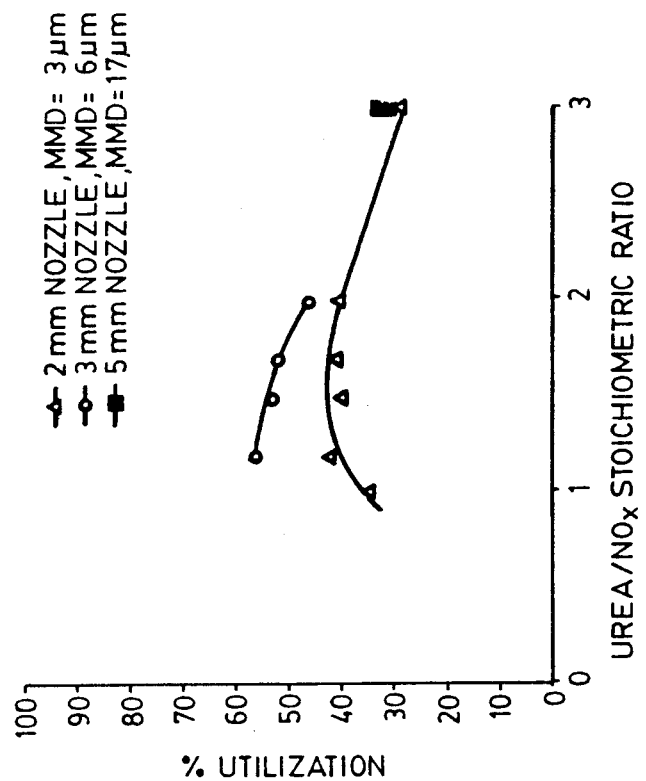
Figure 10A:
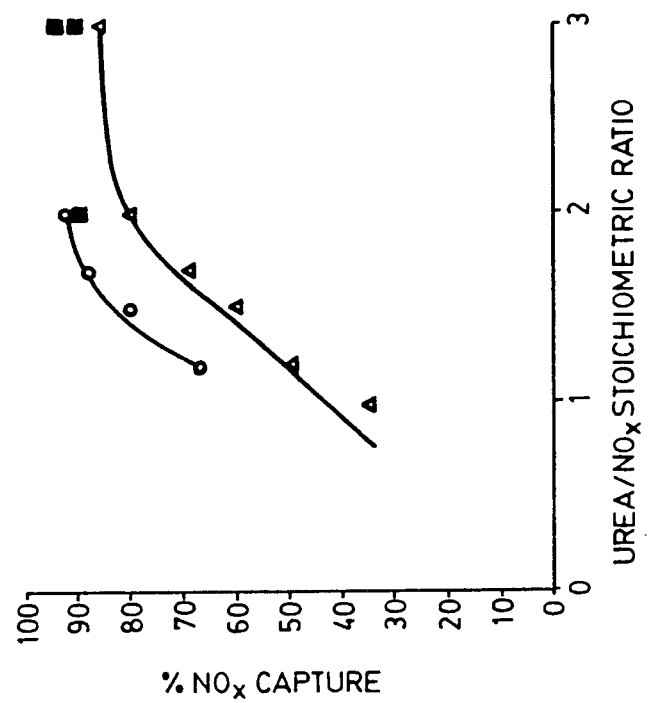
Figure 11:
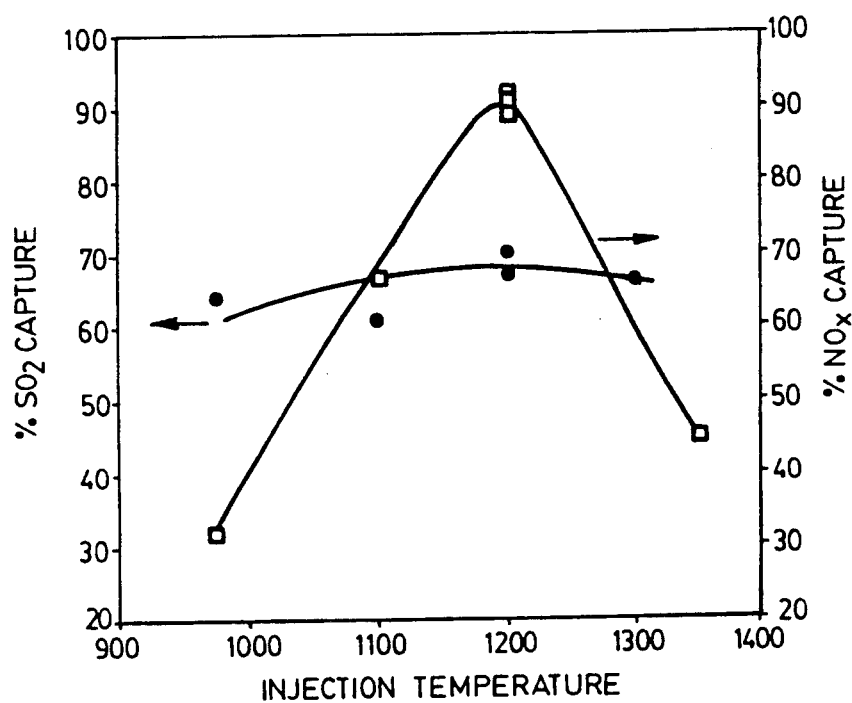
Figure 12:
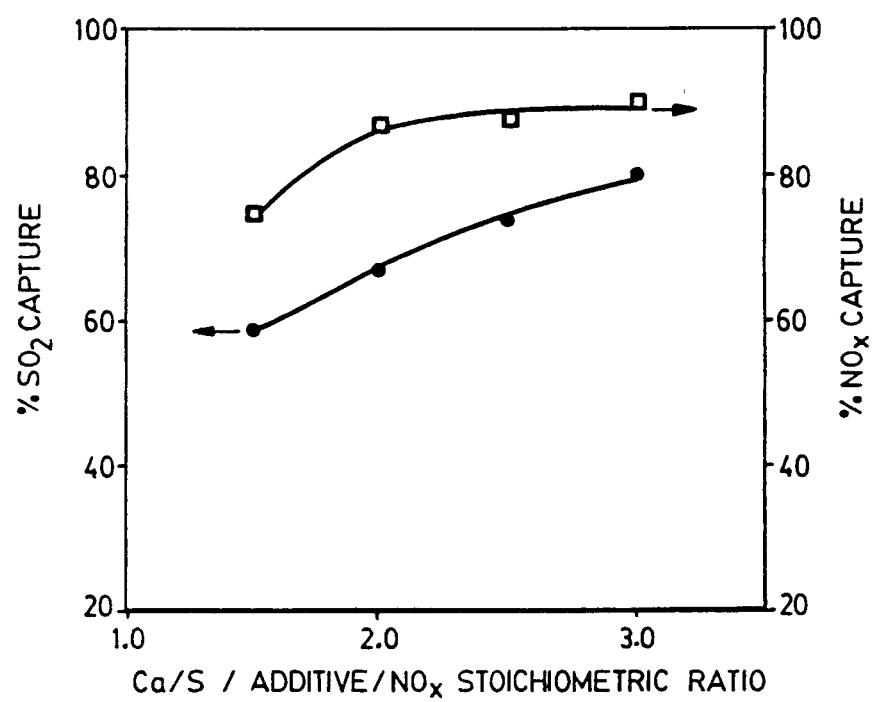
Figure 13:
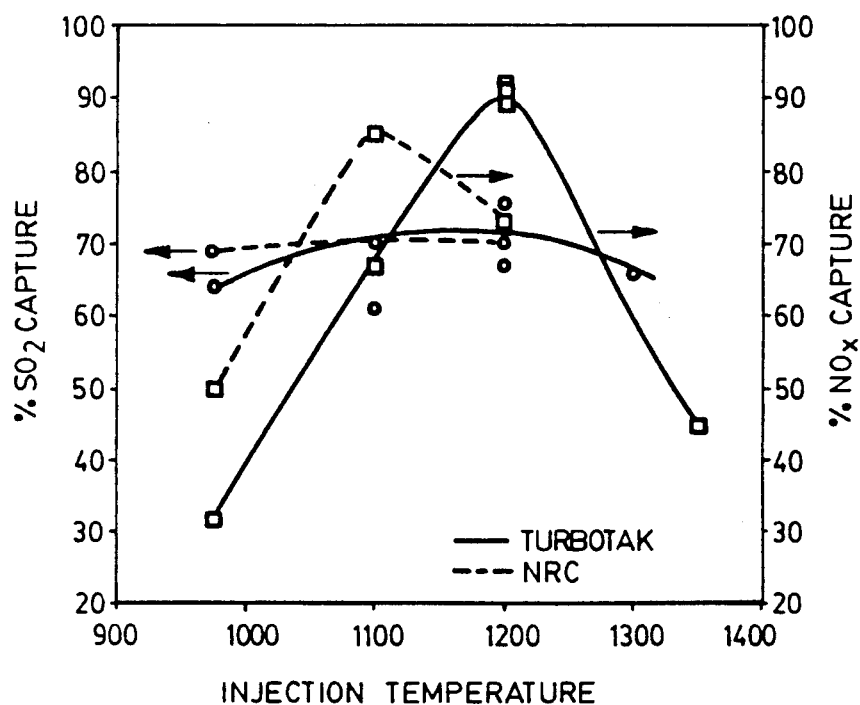
Figure 14B:
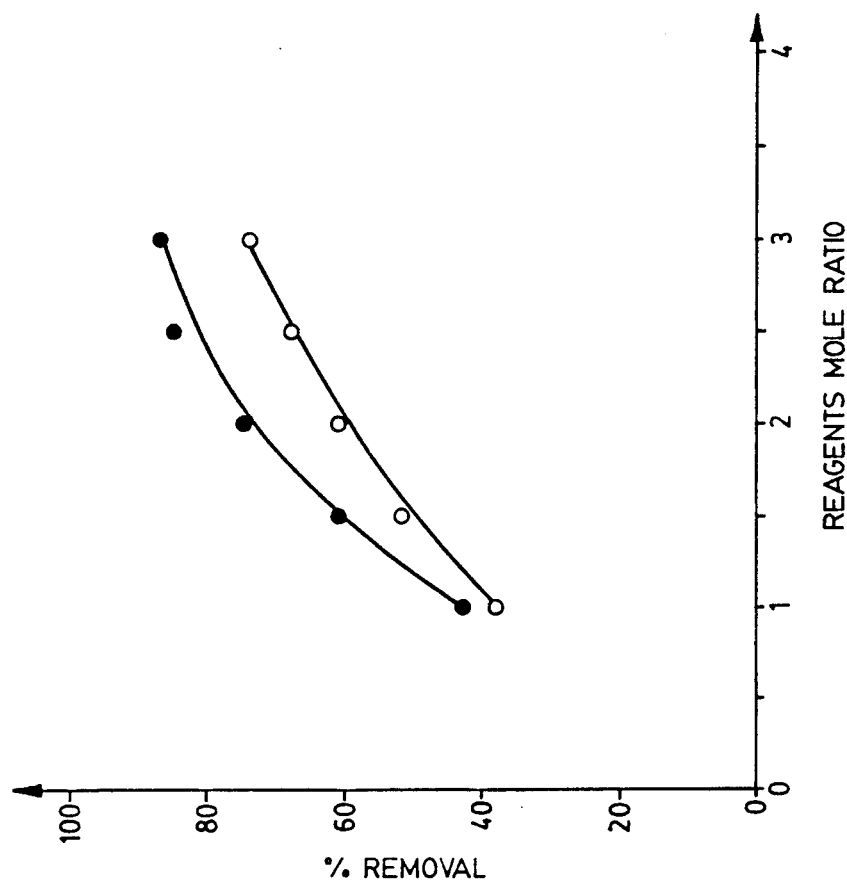
Figure 14A:
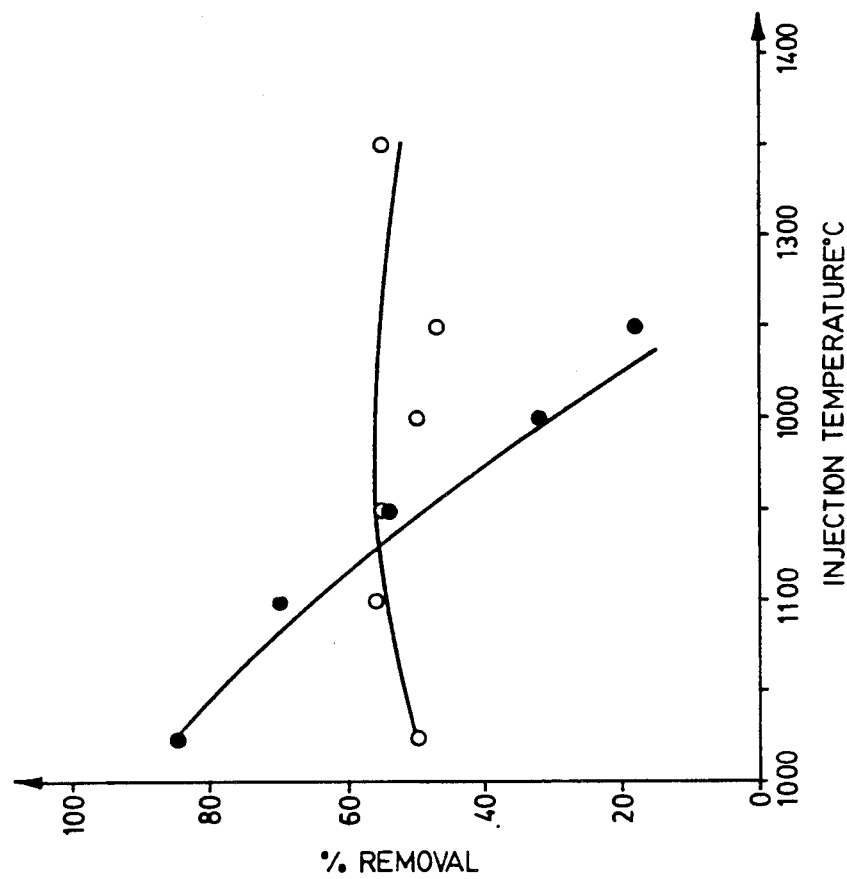
Figure 15B:
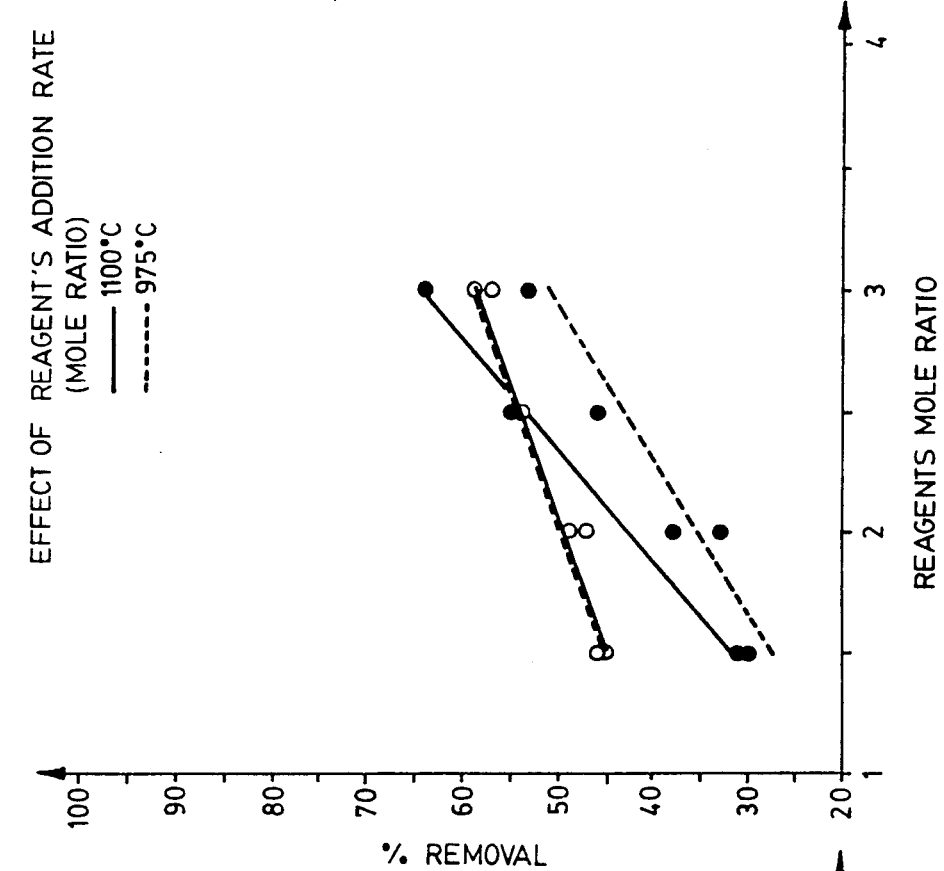
Figure 15A:
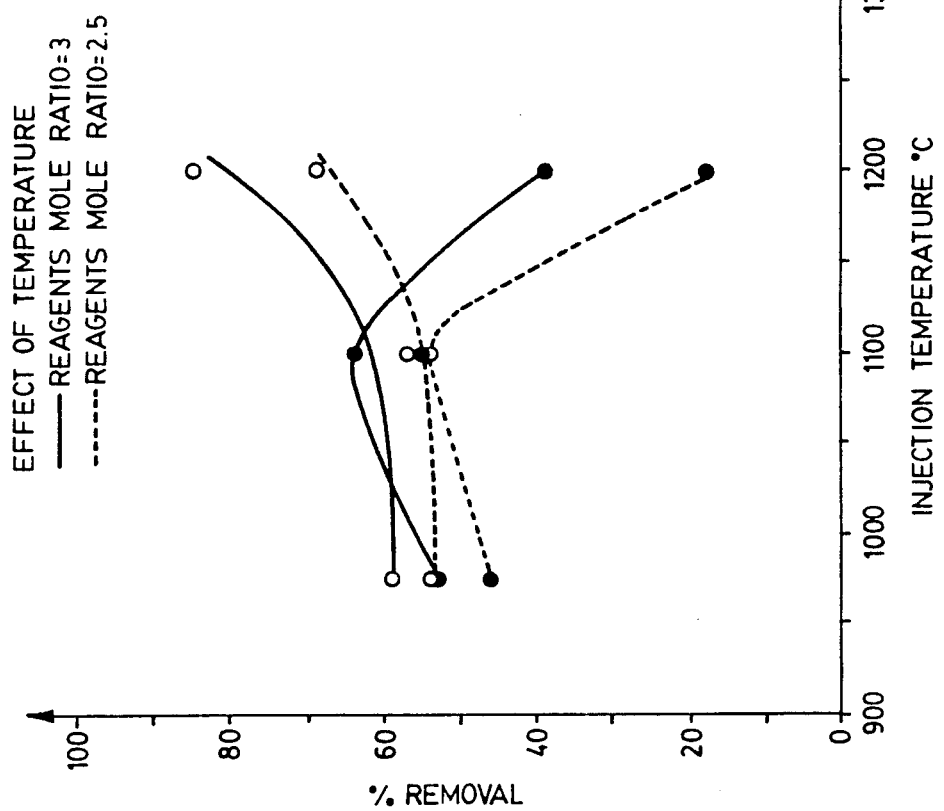

FIG. 4a graphically represents the dependents of limestone slurry droplet size on the atomizing nozzle air pressure and FIG. 4b the dependence of the percentage of $SO_2$ captured on slurry droplet sizes;

FIG. 5 is a graphical representation of the effect of sorbent porosity on the percentage of $SO_2$ captured by an atomized limestone slurry;

FIG. 6a is a graphical presentation of data showing the effect of certain doping agents added to limestone sorbent in enhancing the percentage of $SO_2$ removal and FIG. 6b graphically presents the related percentage of sorbent utilization;

FIG. 7a is a graphical presentation of data showing the variation of $SO_2$ capture with the rate of addition of sorbent and FIG. 7b graphically presents data showing sorbent utilization with the rate of addition of sorbent, said rate of addition being given as the Ca/S ratio;

FIGS. 8a and 8b are graphical presentations of data showing the effect of injection temperature and modes of injection, countercurrent and co-current, respectively, on $SO_2$ capture, for an atomized limestone absorbent slurry;

FIG. 9 is a graphical presentation of data showing the effect of injection temperature on removal of $NO_x$ from flue gas using an atomized urea solution;

FIG. 10a is a graphical presentation of data showing the effect of varying the rate of addition of atomized spray of urea solution on the percentage of $NO_x$ capture and FIG. 10b presents data showing the effect of said varying rate of addition on the utilization of urea;

FIG. 11 is a graphical presentation of the variation of $SO_2$ capture and $NO_x$ capture with temperature using the integrated process of the invention with a limestone sorbent for $SO_2$ capture and urea for $NO_x$ capture;

FIG. 12 is a graphical presentation of the variation of $SO_2$ capture and $NO_x$ capture with the Ca/S and urea/$NO_x$ ratios, respectfully, using a dolomite-limestone sorbent with urea additive injected at 1200° C.;

FIG. 13 is a graphical comparison of the experimental results presented in FIG. 11 with further experimental data on the integrated process of the invention, carried out using a different injection nozzle;

FIG. 14a a is a graphical presentation of data showing the effect of injection temperature on the percentage removal of $SO_2$ and $NO_x$ from flue gas, using ammonium carbonate as the nitrogenous progenitor additive to dolomite-doped limestone sorbent in the process of the invention and FIG. 14b graphically presents the effect of variation of the mole ratios of Ca/S and $(NH_4)_2CO_3/NO_x$ on the percentage removal of $SO_2$ and $NO_x$; and FIG. 15a and 15b are graphical presentations of data showing, respectively, the effect of injection temperature and the effect of reagent mole ratio on the removal of $SO_2$ and $NO_x$ removal, as in FIG. 14a and 14b, but with ammonia as the nitrogenous progenitor additive.

FIG. 1 is a schematic diagram representing sorbent slurry injection in a coal-fired furnace installation. Sorbent slurry containing dissolved additive is injected through nozzle 10 by a stream of air or steam. The injection is made into the combustion chamber at a location removed from burner zone 12, such that the injection temperature is between 900° C. and 1350° C.

The injection mode illustrated in FIG. 1 is "crosscurrent", that is, the direction of injection is across the flow of flue gases, but nozzle 10 can alternatively be directed in the direction of flue gas flow (cocurrent) or against the flue gas flow (countercurrent) towards the higher temperature zone, with significantly differing results, as discussed below.

The flue gases, carrying sorbent particles along, proceed through air heater 14 where some of the thermal energy of the hot flue gas is given up in a heat exchange process and used to heat air returned to the burner zone for further fuel combustion. The flue gas thence proceeds to an electrostatic precipitator (ESP) 16 or bag house filter for removal of solid waste components. The solid waste is composed of fly ash intimately mixed with reaction products, namely $CaSO_4$ and unreacted sorbent, CaO. Although the process of the invention produces about twice as much solid waste as coal ash alone, little problem with efficient ESP collection of particulate is to be expected in practice, because of the lower resistivity of resulting ash, as compared with that produced by injection of dry sorbents. The cleaned flue gases are finally vented through stack 18.

The physical and chemical processes which occur in the course of the process may be summarized as follows:

The finely atomized slurry injected into the furnace loses its water to evaporation very rapidly and the sorbent is calcined into a porous, well-dispersed reactive calcine: $CaCO_3 \rightarrow CaO + O_2$. Under favourable conditions of temperature and residence time, sulphur is captured by the calcine: $CAO + SO_2 + \frac{1}{2}O_2 \rightarrow CASO_4$.

Proceeding along with the above reactions is the thermal generation of amine radicals from the additive, $RNH_x + 2OH \rightarrow 2NH_2 + CO_2 + H_2O$, and capture and removal of NO by the $NH_2$ radicals: $NO + NH_2 \rightarrow N_2 + H_2O$. The hydroxyl radicals OH in the first reaction are generated in the combustion of fossil fuel.

In view of prior publications describing the effectiveness of ammonia or ammonia precursors as agents for the removal of $NO_x$ from gas streams, a number of such materials were investigated as potential slurry additives for an integrated system. These initial attempts invariably met with limited success, in that the $NH_3/NO_x$ reaction was found to be very much less efficient in the presence of calcium-based sorbents for $SO_2$ in the temperature ranges investigated, for reasons that are not entirely clear. The dispersal of particulate sorbent in aqueous ammonia or ammonium carbonate solution was found to give rise to considerable ammonia "slippage" through the furnace at those temperatures. Not only was the efficiency of $NO_x$ removal thereby reduced, but vented $NH_3$ could foul the boiler and is itself an atmospheric pollutant.

Unlike certain $NO_x$ removal agents which were investigated, we have found that selected compatible additive/$NO_x$ and sorbent/$SO_2$ reactions are not subject to interfering side reactions and apparently proceed substantially independently. With such additives and with the slurry injection made in the proper temperature "window", the particular choice of calcium-based sorbent and its concentration in the slurry are important determinants of the efficiency of $SO_2$ removal, but were not observed to have any significant effect on $NO_x$ removal, all other experimental parameters being equal. Likewise, the concentration of compatible additive in the aqueous slurry of sorbent, an important determinant for $NO_x$ removal, appears to have no significant effect on the degree of reduction of $SO_2$ over the ranges investigated.

As noted above, however, integration of $SO_2$ and $NO_x$ removal requires that the respective decontaminating reactions be subject to mutually compatible optimum operating conditions. This we have found to be the case for the additive/limestone aqueous slurry in the process according to the present invention.

Description of Combustion Apparatus and its Operation

The coal-fired furnace installation used to obtain the experimental results discussed herein was Ontario Hydro's Combustion Research Facility (CRF) designed for a maximum coal feed rate of about 20kg/h US bituminous coal at a firing rate of 640 MJ/h. The furnace is a refractory-lined cylindrical chamber, fully equipped for monitoring gas and wall temperatures. There are multiple ports for flame observation and for insertion of solid sampling probes. The pulverized coal is delivered downdraft to the burner with the combustion air which can be electrically preheated to temperatures up to 350° C. (662° F.). Gas burners on each side of the coal burner are used to heat the furnace to operating temperatures before beginning to feed the coal.

The coal burner is equipped with a vortex generator and four air vanes to assure good mixing and adequate residence time of the fuel-air mixture in the combustion zone. The combustion gases in the furnace are cooled by water and/or air circulating in a cylindrical Inconel jacket around the furnace. This cooling system is equipped with temperature sensors and flow meters to control furnace quenching rates.

The combustion gases leaving the furnace are further cooled by a series of air-cooled heat exchangers prior to entering the resistivity probe housing and ESP. The ESP consists of a cubic stainless steel chamber, and is equipped with two sets of interchangeable cells. One set has an 11-plate electrode with 2.5 cm (1 in) spacing, the other a 5-plate electrode with 5 cm (2 in) spacing. The design specific collection areas (SCA, $m^2/m^3/s$) for the two sets of cells are 39 (0.2 $ft^2$/cfm) and 17 (0.09 $ft^2$/cfm) respectively for baseline firing conditions using a high volatile US bituminous coal.

The CRF instrumentation permits system temperatures, and flue gas compositions ($O_2$, $CO_2$, CO, $SO_2$ and $NO_x$) to be monitored continuously. Gas temperatures in the furnace were measured with a suction pyrometer and flame temperatures with an optical pyrometer. Flow rates and pressures are measured by flow meters and manometers. All measuring and monitoring systems are linked to a computerized data acquisition system. Particulate mass loading in the flue gas before and after the ESP is measured with an isokinetic sampling system and particle size distribution of fly ash and wastes are measured with a cascade impactor. In-situ resistivity is measured with a point-plane resistivity probe situated in the resistivity probe housing.

Figure 2:
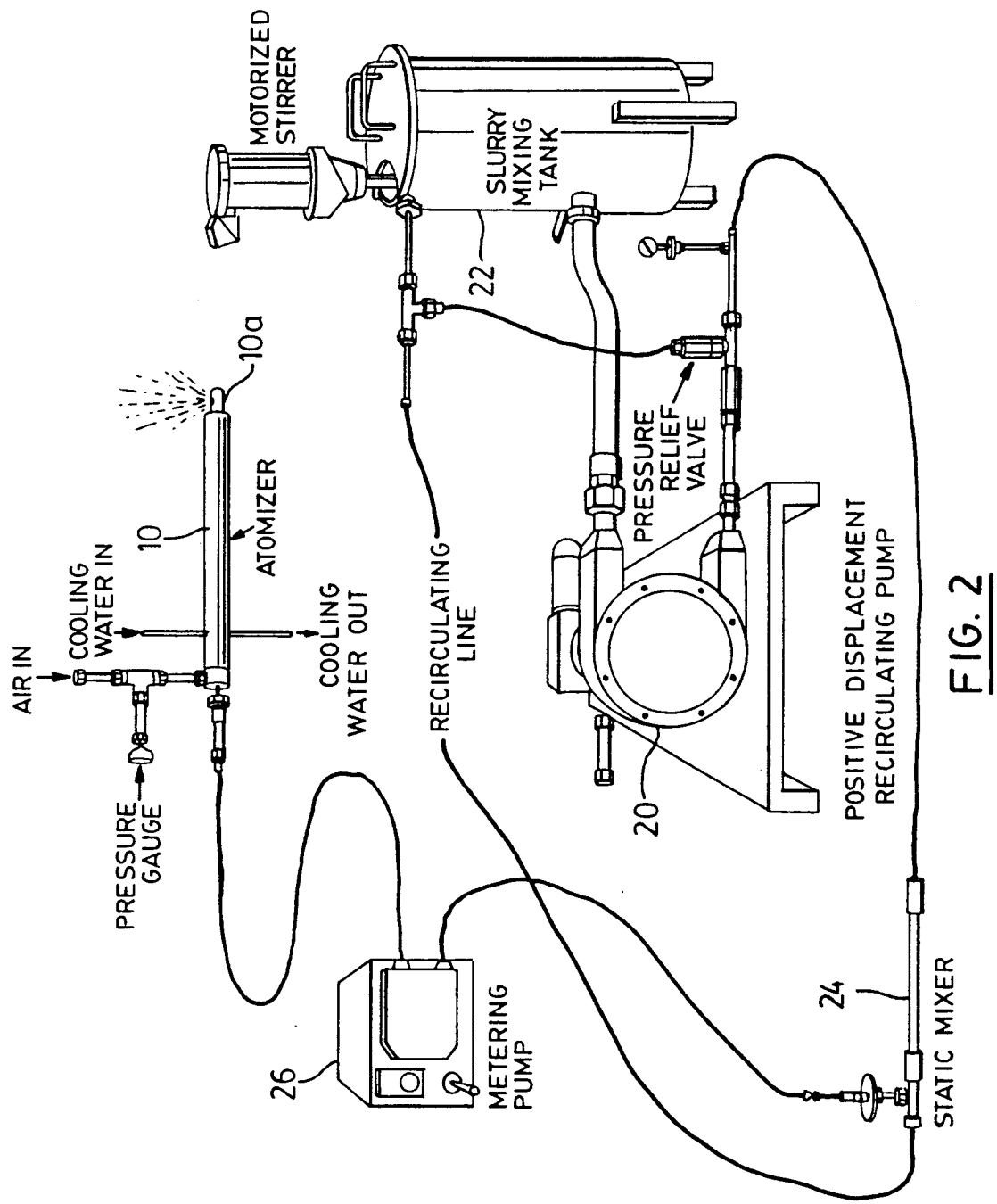
FIG. 2 illustrates the slurry injection system which was used to inject a sorbent slurry into the coal-fired pilot furnace installation used in carrying out and experimentally evaluating the process of the invention.

The slurry injection system used in carrying out the process of the invention in the CRF experimental installation is shown in FIG. 2. The injection system consists of a positive displacement pump 20 which pumps L the slurry from a continuously stirred mixing tank 22 under a pressure of 94 to 104 psig. Slurry recirculation and a static mixer 24 upstream of the furnace keep the fine sorbent particles in suspension and prevent settling. A small metering pump 26 delivers the slurry to the atomizer nozzle 10 through which fine droplets are injected into the flue gas stream.

The structure of the atomizer nozzle used in the injection system of FIG. 2 is shown in greater detail in FIG. 3. The slurry is injected into the middle of the furnace through this high pressure twin-fluid nozzle 10 (5, 3 or 2 mm) with an internal mixing chamber 28. Operating pressures range between 40 and 70 psig. The stainless steel nozzle tip 10a (purchased from Turbotak Inc.) produces droplets of about 17 μm MMD for a 5 mm nozzle tip, 6 μm for a 3 mm nozzle tip and 3 μm for a 2 mm nozzle tip. The nozzle is equipped with a cooling jacket 30 which is necessary to avoid drying of the slurry and deposition of particles in the nozzle.

As illustrated schematically in FIG. 1, the aqueous slurry of sorbent and urea additive was injected into the middle region of the furnace, where a selected injection temperature of between about 900° C. and about 1400° C. could be achieved. Slurry without added urea or aqueous urea solution alone were injected through nozzle 10 in preliminary experiments, to study the non-integrated $SO_2$ and $NO_x$ removal processes, respectively.

In-furnace Injection of Calcium based Sorbent Slurries

The parameters affecting $SO_2$ removal in the absence of nitrogenous progenitor additive were studied by injecting slurries of two different Ontario calcitic limestones and a dolomite to remove $SO_2$ from flue gases while burning a 1.7% sulphur Eastern U.S. bituminous coal. Also evaluated was sorbent injection using two other coals: a 1.5% sulphur blend of Eastern U.S. and Western Canadian coals and a 2.8% sulphur Nova Scotia coal. A Nova Scotia Mosher limestone slurry was used to remove $SO_2$ from the Nova Scotia coal. All results were obtained using the above-described Ontario Hydro Combustion Research Facility.

Slurry droplet size was found to be an important parameter in determining the efficiency of $SO_2$ removal by sorbent slurry injection. Fine droplets are desirable to provide high sorbent surface area of the Ca based sorbents and good distribution and mixing of the reagents with the flue gases. If the droplets are too fine, however, the penetration of sorbents into the furnace is inadequate and their mixing with the flue gases is poor, resulting in diminished $SO_2$ removal. FIGS. 4a and 4b present the results of measurements made using the Turbotak nozzle and a 40% aqueous slurry of finely pulverized Pt. Anne limestone at a molar ratio of Ca (from sorbent) to S (from the coal), "Ca/S", equal to 3.0, a slurry flow rate of 70 ml/min and an injection temperature of 1200° C. Optimum droplet size was found to be about 5–7 $\mu$m. The coal/sorbent types tested were U.S. coal with Pt. Anne limestone (open circle data points), a mixture of U.S. and Western Canadian coal with Pt. Anne limestone (diamonds), Nova Scotia coal with Nova Scotia limestone (triangles) and U.S. coal with Beachville limestone (squares).

Sulphur capture efficiency by limestone slurry injection was found to improve with increasing limestone porosity, as shown graphically in FIG. 5. A 40% aqueous slurry of limestone with an approximate porosity of 50 per cent achieved 70% $SO_2$ removal at a Ca/S ratio of 3 (solid line) while under the same conditions (injection temperature 1200° C., co-current injection mode and droplet MMD of 6 $\mu$m) the limestone with a 17% porosity captured only 55% of the $SO_2$ line). The coal burnt in the pilot furnace installation was a U.S. coal with 1.7% sulphur content.

Dolomite was found to be a more effective sorbent than limestone, for a given Ca/S ratio. At similar operating conditions, $SO_2$ capture by dolomite with a porosity of 42% was 83%. However, the CaO content of dolomite is so low that its use alone as the sorbent would require the injection of too much slurry, increasing the dust loading effect to a point which could impair operation of the ESP.

A number of limestone additives were tested as agents for enhancing desulphurization. The additives tested include dolomite, sodium hydroxide and hydrated lime, which were used to dope Pt. Anne limestone. A chosen fraction of the calcium from the limestone was replaced by an equivalent amount of the additive, thereby to maintain the same Ca/S stoichiometry as for the undoped (baseline) case. The experimental results are presented in the graphs of FIGS. 6a and 6b, from which it is apparent that the dolomite-doped Pt. Anne limestone was the most effective in enhancing sulphur capture. Injection temperature and mode and droplet size were the same as for the run without doping (FIG. 5). Plots of %$SO_2$ removal and %Ca utilization are shown, the latter being a measure of the efficiency of the sorbent/$SO_2$ reaction for a given sorbent composition and rate of sorbent addition.

Replacing 10% of the calcium from the Pt. Anne limestone with dolomite improved $SO_2$ capture from 70% to 80% and calcium utilization from 23% to 27% for a Ca to S ratio of 3.0, as seen in FIGS. 6a and 6b. At a ratio of 2.0, $SO_2$ capture improved from 53 to 67% and Ca utilization from 27 to 34%. The other aforementioned additives ranked in decreasing order of sulphur capture enhancement are sodium hydroxide and hydrated lime. Since dolomite is the most cost-effective of the additives and was found to perform better than the others in enhancing sulphur capture and in improving calcium utilization, dolomite-doped limestone would appear to be the sorbent of choice for slurry removal of $SO_2$ emissions from utility boiler flue gases.

Sulphur capture was found to decrease with decreasing Ca/S ratio, i.e. decreasing rate of addition of sorbent, for all coal/sorbent pairs tested, while sorbent utilization increased. The results shown in the graphs of FIGS. 7a and 7b were obtained by the co-current injection of a 40% aqueous slurry of sorbent using the Turbotak 3 mm nozzle to produce a droplet size of 6 $\mu$m MMD. For the porous Pt. Anne limestone (PA), reduction of the Ca/S ratio from 3 to 1.5 resulted in a drop in $SO_2$ capture from 70% to 50%. With dolomite, $SO_2$ capture for the 3 and 1.5 Ca/S ratios were 83% and 75%, respectively. In FIGS. 7a and 7b, the open circle data points relate to an injection temperature of 1200° C. and the closed circles 1300° C. "B", "US" "USWC", "D" and "NSC" stand for Beachville limestone, U.S. coal, U.S.-Western Canadian coal blend, dolomite and Nova Scotia coal, respectively.

Other measurements on sorbent-only slurries showed sulphur capture to be a sensitive function of the injection mode and temperature at the injection site, FIGS. 8a and 8b. The data points in FIGS. 8a and 8b relate to specific combinations of coal and limestone having various Ca/S ratios as indicated in Table 1:

TABLE 1

| | COAL | % S | LIMESTONE | Ca/S RATIO |
|---|---|---|---|---|
| • | U.S. | 1.7 | PT. ANNE | 3.0 |
| | U.S. | 1.7 | BEACHVILLE | 3.0 |
| | U.S.-WC | 1.5 | PT. ANNE | 3.0 |
| ○ | NOVA SCOTIA | 2.8 | NOVA SCOTIA | 3.2 |
| | NOVA SCOTIA | 2.8 | PT. ANNE | 3.0 |
| □ | U.S. | 1.7 | DOLOMITE | 1.5–3.0 |

40% LIMESTONE SLURRY (PT ANNE AND BEACHVILLE)
20% NOVA SCOTIA LIMESTONE SLURRY
DROPLET SIZE — 6 $\mu$m MMD (TURBOTAK 3 mm NOZZLE)

Nova Scotia limestone was injected at a Ca/S ratio of 2.2. Only the co-current injection mode was used with the dolomite and the U.S. coal. A nozzle with a 3 mm orifice, and in a few cases with a 5 mm orifice producing droplets of 6 $\mu$m and 17 $\mu$m MMD, respectively, were used. The $SO_2$ content of the flue gas before and after injection was recorded, and the results are presented in the graphs of FIGS. 8a and 8b. As illustrated in these graphs, the optimum injection temperature for the cocurrent injection with all the coals and limestone tested was around 1200° C., while for the counter-current injection, around 1100 C. The lower optimum for the counter-current mode of injection arises from the fact that the slurry is in that mode injected toward the high temperature region of the furnace. Thus, the slurry injected at 1200° C. actually "sees" high temperatures where sintering and deadburning occurs and sulphur capture is less efficient. In either the counter-current or the co-current injection mode, sulphur capture was seen to drop by raising or lowering the injection temperature from the optimum.

Optimum sulphur capture with all coals and limestone studies was significantly higher for the co-current injection than for counter-current injection, the highest $SO_2$ capture of 83% being observed with dolomite. At temperatures below about 900° C. or above about 1350° C., $SO_2$ capture falls off considerably to unacceptably low levels for both injection modes and all sorbents investigated, as seen from the graphs of FIGS. 8a and 8b.

In all of the separate and integrated runs whose results are presented herein, the furnace quenching rate was kept at 500° C./s to simulate existing Ontario Hydro power plant units. One test was done in which the quenching rate was changed from 500° C./s to 280° C./s, thereby increasing the residence time for the slurry in the effective sulphation zone (900–1350° C.) from 600 ms to 900 ms. No significant change in $SO_2$ capture was observed, however, by contrast with prior known techniques for the in-furnace injection of dry limestone, for which an increase in residence time in the sulphation zone significantly improves sulphur capture. The reason for the relative insensitivity of the slurry injection is probably the fast reaction rate between limestone slurry and $SO_2$ In-furnace Injection of Aqueous Urea Solution Of the nitrogen-based additives tested for integration with $SO_2$ removal, urea appeared to be the most effective in reducing $NO_x$ concentrations in flue gases. It is soluble in the sorbent slurry, the injection temperatures for optimum $SO_2$ and $NO_x$ removal coincide, and the $SO_2$ and $NO_x$ capture reactions do not interfere with each other. In order to assess the potential for integration of urea as an additive to limestone slurry, a number of preliminary investigations were made of the parameters affecting $NO_x$ removal alone, by injecting urea solutions in the absence of calcium-based sorbents.

As with the removal of $SO_2$ by sorbent slurry alone, the mode of injection of urea solution into the furnace and the temperature at the injection location were found to be important determinants of $NO_x$ removal efficiency. Experimental results obtained are graphically illustrated in the plot of percentage $NO_x$ removal versus injection temperature given in FIG. 9, the solid graph lines relating to co-current injection and the two lower broken-line graphs to counter-current injection. A 13.5% aqueous solution of urea was injected through a Turbotak nozzle, the size of the droplets being 17 μm MMD. The fuel burned was a 17%S U.S. Eastern bituminous coal. The urea solution was injected either cocurrently or counter-currently to the gas flow at stoichiometric ratios of either 2 or 3, as indicated in the legend on the graphs.

A comparison of these results with those discussed above in connection with FIG. 8a and 8b led to the hope that the co-current injection mode might prove suitable for integrating urea additive with sorbent slurry, since the injection temperature of 1100–1200° C. for maximum $NO_x$ capture was the same as for maximum $SO_2$ capture by the in-furnace injection of limestone slurry. At optimum temperature using co-current injection, $NO_x$ capture was seen to be 90% compared to less than 30% for the countercurrent mode.

An important consideration for full scale application of an integrated process is that the attainment of 90% $NO_x$ capture afforded a temperature window of only about ±50° C. If an 80% $NO_x$ capture is considered sufficient, that window widens to about ±150° C.

The removal of $NO_x$ by urea injection was also evaluated as a function of urea stoichiometry, i.e., the rate of addition of urea. The urea/$NO_x$ stoichiometric ratio was varied from 1 to 3 and variously injected into the furnace using 2 mm, 3 mm and 5 mm Turbotak nozzles producing droplets of size 3, 6 and 17 μm MMD. 13.5% aqueous urea solution was injected at 1100 C. in the cocurrent mode. The fuel firing the burner was a 1.7% sulphur Eastern U.S. bituminous coal. The experimental results are set out in the graphs of FIGS. 10a and 10b, respectively showing the percentage $NO_x$ capture and the percentage utilization of urea as functions of the urea/$NO_x$ stoichiometric ratio. $NO_x$ capture by the urea stoichiometry of 3 and 1.5 for the 3 mm nozzle were 90 and 80%, respectively and utilizations were 30 and 53%, respectively.

Integrated $SO_2$–$NO_x$ Removal with Urea Additive

EXAMPLE 1

Simultaneous capture of $SO_2$ and $NO_x$ was undertaken by adding urea to an aqueous slurry of limestone and adjusting operating conditions for the optimum capture of each pollutant, on the basis of the above-described results for the separate sorbent/$SO_2$ and urea/$NO_x$ processes.

FIG. 11 is a plot of the measured $SO_2$ and $NO_x$ percentage captured as a function of temperature for the following optimized operating conditions:

a 40% aqueous solution of a porous Pt. Anne limestone slurry
Ca/S ratio=3.0
urea concentration of 13.5% in slurry
urea/$NO_x$ ratio=2.0
injection mode: co-current
nozzle: Turbotak 3 mm, droplet size MMD, 6 μm.

The square data points relate to %$NO_x$ capture and the filled circles to %$SO_2$ capture.

The fuel was the same 1.7%S U.S. bituminous coal which was the subject of studies on the individual $SO_2$ and $NO_x$ removal processes. The results show successful integration—the removal of up to 70% of the $SO_2$ and 90% of the $NO_x$ if the limestone slurry additive is injected at 1200° C.±50° C. $NO_x$ capture drops very sharply at both higher and lower injection temperatures. $SO_2$ capture has a much wider temperature window. As noted above, if a wider temperature window is required in order to ease full scale operation, up to 65–70% $SO_2$ capture and 80–90% $NO_x$ capture is achievable in an operating window of 1130 to 1280° C.

EXAMPLE 2

Simultaneous capture of $SO_2$ and $NO_x$ was carried out using a different sorbent than in Example 1, namely 15% dolomite-doped limestone injected co-currently at 1200° C. The rate of addition of sorbent to the combustion chamber, measured as the Ca/S ratio, was varied. In FIG. 12, the percentage of $SO_2$ capture (circular data points) and the percentage of $NO_x$ capture (square data points) are shown as functions of the Ca/S ratio and urea/$NO_x$ ratio. Under the aforesaid experimental conditions and at a Ca/S ratio of 3.0, simultaneous removal of about 90% of $NO_x$ and about 80% of $SO_2$ were removed from the flue gas, representing a very satisfactory degree of decontamination in respect of both pollutants.

EXAMPLE 3

In order to compare the simultaneous removal of pollutants according to the integrated process of the invention with the separate removal of $NO_x$ and $SO_2$ carried out under like experimental conditions, the two stoichiometric ratios in the integrated process were adjusted in concert. The results are set out in Table 2:

TABLE 2

|     | Ca/S | Urea/NO$_x$ | % SO$_2$ removal | % NO$_x$ removal |
| --- | --- | --- | --- | --- |
| (a) | 1.5 | — | 62 | — |
| (b) | — | 1.5 | — | 81 |
| (c) | 1.5 | 1.5 | 59 | 75 |
| (a) | 2.0 | — | 67 | — |
| (b) | — | 2.0 | — | 89 |
| (c) | 2.0 | 2.0 | 67 | 88 |
| (a) | 3.0 | — | 80 | — |
| (b) | — | 3.0 | — | 90, 91, 92 |
| (c) | 3.0 | 3.0 | 78 | 90 |

The indices "a", "b", and "c" to the left of the table refer in each case to injection of sorbent slurry alone, urea solution alone, and the integrated slurry, respectively. In each instance, the slurry was introduced by co-current injection through a Turbotak nozzle (6 µm MMD droplet size), at an injection temperature of 1200° C. The furnace was fired with 1.7% sulphur U.S. coal and the sorbent employed was the 15% dolomite-doped limestone of the previous example, which was noted to have produced the best overall results.

Comparisons are made at Ca/S and urea/NO$_x$ stoichiometric ratios of 1.5, 2.0 and 3.0. Within experimental error, the efficiency of NO$_x$ removal and SO$_2$ removal in the integrated system are unchanged from their independent pollutant removal efficiencies. This demonstrated substantial independence of the sorbent-/SO$_2$ and urea/NO$_x$ reactions, in conjunction with mutually compatible optimum parameters such as injection temperature, injection mode etc., is the basis for the first genuinely integrated process for the simultaneous capture of both pollutants.

EXAMPLE 4

The graph of FIG. 13 includes the Example 1 data of FIG. 11 (solid curves) but shows in addition the data points obtained when a different nozzle ("NRC") than the Turbotak was employed. Again, the square data points refer to NO$_x$ capture, the solid circles to SO$_2$ capture. optimum injection temperature for both SO$_2$ and NO$_x$ capture from about 1200° C. to about 1100° C., owing to differences in spray characteristics between the two nozzles. The results are illustrative again, however, of the truly integrated character of the process of the invention, since SO$_2$ and NO$_x$ removal may be simultaneously optimized using either nozzle.

Integrated SO$_2$–NO$_x$ Removal with Ammonium Carbonate Additive

The experimental data presented in the table below and graphically summarized in FIGS. 14a and 14b show that as a nitrogenous progenitor additive ammonium carbonate (AC) in an aqueous slurry of limestone is almost as efficient as urea for removing NO$_x$ from flue gases simultaneously with the removal of SO$_2$.

TABLE 3

| SONOX PROCESS - SO$_2$—NO$_x$ REMOVAL | | | | | | | |
| --- | --- | --- | --- | --- | --- | --- | --- |
| Sorbent-Additive 40% Aqueous Slurry | Addition Rate, Mole | | Inlet Concen. ppm | | Injection Temperature | % Removal | |
| | Ca/S | AC/N | SO$_2$ | NO$_x$ | | SO$_2$ | NO$_x$ |
| A. Effect of Temperature | | | | | | | |
| LS/D-AC | 2.0 | 2.0 | 1100 | 630 | 1350 | 55 | |
| | | | | | 1250 | 47 | 18 |
| | | | | | 1200 | 50 | 32 |
| | | | | | 1150 | 55 | 54 |
| | | | | | 1100 | 56 | 70 |
| | | | | | 1025 | 50 | 85 |
| LS-AC | 3.0 | 2.0 | 955 | 495 | 1200 | 62 | 55 |
| | | | | | 1100 | 66 | 46 |
| | | | | | 975 | 62 | 65 |
| LS-AC | 2.0 | 2.0 | 1155 | 588 | 1200 | 70 | 71 |
| | 1.7 | 1.7 | | | 1200 | 64 | 63 |
| LS-A | 3.0 | 3.0 | 1280 | 598 | 1200 | 85 | 39 |
| | | | | | 1100 | 57 | 64 |
| | | | | | 975 | 59 | 53 |
| | 2.5 | 2.5 | | | 1200 | 69 | 18 |
| | | | | | 1100 | 54 | 55 |
| | | | | | 975 | 54 | 46 |
| B. Effect of Sorbent-Additive Addition Rate | | | | | | | |
| LS/D-AC | 1.0 | 1.0 | 1100 | 630 | 1100 | 38 | 43 |
| | 1.5 | 1.5 | | | | 52 | 61 |
| | 2.0 | 2.0 | | | | 61 | 75 |
| | 2.5 | 2.5 | | | | 68 | 85 |
| | 3.0 | 3.0 | | | | 74 | 87 |
| LS-A | 3.0 | 3.0 | 1280 | 598 | 1100 | 57 | 64 |
| | 2.5 | 2.5 | | | | 54 | 55 |
| | 2.0 | 2.0 | | | | 49 | 38 |
| | 1.5 | 1.5 | | | | 45 | 30 |
| | 3.0 | 3.0 | | | 975 | 59 | 53 |
| | 2.5 | 2.5 | | | | 54 | 46 |
| | 2.0 | 2.0 | | | | 47 | 33 |

TABLE 3-continued

SONOX PROCESS - $SO_2$—$NO_x$ REMOVAL

| Sorbent-Additive 40% Aqueous Slurry | Addition Rate, Mole | | Inlet Concen. ppm | | Injection Temperature | % Removal | |
|---|---|---|---|---|---|---|---|
| | Ca/S | AC/N | $SO_2$ | $NO_x$ | | $SO_2$ | $NO_x$ |
| | 1.5 | 1.5 | | | | 46 | 31 |

LS/D = Pt. Anne Limestone doped with 10% dolomite
AC = Ammonium carbonate
LS = Pt. Anne Limestone
A = Ammonia The data on simultaneous removal of $SO_2$ and $NO_x$ with limestone slurry and ammonium carbonate under optimized operating conditions according to the invention indicate that with an injection temperature of about 1100° C., a Ca/S ratio in the range of 2.5–3 and an AC/$NO_x$ ratio of between about 2 and 2.5, $SO_2$ removal is up to 75% and $NO_x$ removal is up to 85%.

FIG. 14a shows the variation with injection temperature of $SO_2$ removal (open circle data points) and $NO_x$ removal (close circle data points) at a fixed molar ratio of Ca/S equal to 2 and a fixed molar ratio of AC./$NO_x$ equal to 2, afforded using a 40% aqueous slurry of dolomite-doped Pt. Anne limestone with ammonium carbonate.

Using the same reagents at a fixed injection temperature of 1100° C., the variation of removal of the two pollutants with increasing Ca/S and AC/$NO_x$ mole ratios is illustrated in FIG. 14b.

Integrated $SO_2$-$NO_x$ Removal with Ammonia Additive

Graphical displays of data analogous to FIG. 14a and 14b for ammonium carbonate additive are given in FIGS. 15a and 15b with ammonia as the additive. A 40% aqueous slurry of Pt. Anne limestone with added ammonia was used. The variation of percentage removal of $SO_2$ (open circles) and $NO_x$ (closed circles) with injection temperature is shown in the graph of FIG. 15a. The darker data lines relate to a reagent mole ratio of 3.0 and the lighter data line to a reagent mole ratio of 2.5 for each of Ca/S and $NH_3$/$NO_x$. In FIG. 15b, using the same sorbent and additive, the percentage removal of pollutants as a function of mole ratio is illustrated at two different fixed injection temperatures, 1100° C. (dark line) and 975° C. (light line).

Under optimized operating conditions, $SO_2$ and $NO_x$ captures of about 58% and 64%, respectively were obtained. Thus, limestone slurry with ammonia was found to be less efficient for removing sulphur and nitrogen oxides than either urea or ammonium carbonate, but still were reasonably efficient for the simultaneous removal of pollutants in the temperature window for sulphation of the calcium-based sorbent.

In summary, the in-furnace injection of a calcium-based sorbent slurry with a compatible nitrogenous progenitor additive, according to the process of the invention has been found to afford a simple and efficient route to the simultaneous removal of $SO_2$ and $NO_x$ from power plant and incinerator flue gas streams. The technique facilitates good distribution and mixing of reagents with the flue gas, prevents the deactivation of sorbent and allows sufficient residence time at favourable temperatures for the CaO/$SO_2$ and additive/$NO_x$ reactions to be completed efficiently. The variables affecting acid gas capture by the process have been identified and optimized for maximum acid gas removal and sorbent utilization using various sorbents with different coals.

The experimental examples are not intended to limit the scope of the present invention, but are illustrative only, and it will be obvious that certain changes and modifications may be practised within the scope of the appended claims. In particular, it will be appreciated that a wide range of nitrogen based compounds (nitrogenous progenitors) will be useful as additives in the integrated process of the invention, since many members of this family will produce reactive species, such as $NH_2$ radicals, for the removal of $NO_x$ in the temperature window of between about 900° C. and about 1350° C. in which the CaO/$SO_2$ reaction takes place, without chemically interfering with the sulphation reaction.

We claim:

1. A process for the simultaneous reduction of the $SO_2$ and $NO_x$ content of flue gas from a fossil fuel fired combustion installation, comprising the step of injecting an atomized aqueous slurry composition into the combustion chamber of the installation at a location having a temperature of between about 900° C. and about 1350° C., said aqueous slurry composition comprising a dispersion in water of a finely particulate, calcium-based sorbent for $SO_2$ and a nitrogenous progenitor compound which produces species reactive with $NO_x$ at said temperature, the concentrations of sorbent and said compound in the slurry composition being respectively selected to provide calcium in the amount of between 1.5 and 3.0 moles Ca per mole of $SO_2$ and said compound in an amount to give a stoichiometric ratio of at least 1.5 moles of nitrogenous progenitor per mole of $NO_x$.

2. A process according to claim 1, wherein said calcium-based sorbent is selected from the group consisting of limestone and mixtures of limestone with dolomite, sodium hydroxide, or hydrated lime.

3. A process according to claim 2, wherein said atomized slurry concentration has a droplet size of up to about 150 μm MMD.

4. A process according to claim 3, wherein said nitrogenous progenitor compound is selected from the group consisting of ammonia, ammonium carbonate and urea.

5. A process according to claim 4, wherein the concentration of said nitrogenous progenitor compound in said aqueous slurry composition is selected to provide said nitrogenous progenitor compound in an amount providing a stoichiometric ratio of between 1.5 and 2.5 moles of nitrogenous progenitor compound per mole of $NO_x$.

6. A process according to claim 4, wherein said nitrogenous progenitor compound is urea 7. A process according to claim 2, claim 3, or claim 4, wherein said atomized aqueous slurry is injected into the combustion chamber in a direction generally co-current with the flow of flue gas.

8. A process according to claim 2, claim 3, or claim 4, wherein said aqueous slurry composition is injected at a temperature of between 1100° C. and 1300° C.

9. A process according to claim 4, wherein said calcium-based sorbent is pulverized limestone intimately mixed with up to 15% by weight of dolomite 10. A process according to claim 2, wherein said nitrogenous progenitor compound is urea and said atomized aqueous slurry composition has a droplet mass median diameter in the range of 3-17 $\mu$m MMD.

* * * * *